(12) United States Patent
Kim et al.

(10) Patent No.: US 9,625,918 B2
(45) Date of Patent: *Apr. 18, 2017

(54) FLUID-PRESSURE REGULATION SYSTEMS AND SOFTWARE

(71) Applicant: Carnegie Mellon University, Pittsburgh, PA (US)

(72) Inventors: Yong-Tae Kim, Pittsburgh, PA (US); Matthew Brandon Kuczenski, Santa Barbara, CA (US); Philip LeDuc, Pittsburgh, PA (US); William Messner, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/857,290

(22) Filed: Sep. 17, 2015

(65) Prior Publication Data

US 2016/0004261 A1    Jan. 7, 2016

Related U.S. Application Data

(63) Continuation of application No. 12/841,743, filed on Jul. 22, 2010, now Pat. No. 9,170,267.
(Continued)

(51) Int. Cl.
*G05D 16/20* (2006.01)
*G01N 35/10* (2006.01)
(Continued)

(52) U.S. Cl.
CPC ....... *G05D 16/202* (2013.01); *G01N 35/1095* (2013.01); *G05B 15/02* (2013.01);
(Continued)

(58) Field of Classification Search
CPC ............. G05D 16/202; G05D 16/2066; G05D 16/2086; Y10T 137/0396;
(Continued)

(56) References Cited

U.S. PATENT DOCUMENTS 2,183,235 A    12/1939    Callender
3,777,778 A    12/1973    Janu
(Continued)

FOREIGN PATENT DOCUMENTS

WO    WO2006044571 A1    4/2006

OTHER PUBLICATIONS

Restriction Requirement dated Sep. 26, 2012, issued in connection with related U.S. Appl. No. 12/841,743, filed Jul. 22, 2010.
(Continued)

*Primary Examiner* — William McCalister
(74) *Attorney, Agent, or Firm* — Downs Rachlin Martin PLLC

(57) ABSTRACT

A fluid-pressure regulator for regulating the pressure of a fluid. The regulator includes a variable-resistance fluid element and a variable-volume fluid element located downstream of the variable-resistance element. Pressure in the fluid at the outlet of the regulator is controlled by substantially simultaneously changing the resistance of the variable-resistance element and the volume of the variable-volume element. In one example, a decrease in pressure is effected at the outlet by simultaneously increasing the resistance of the variable-resistance element and increasing the volume of the variable-volume element. Some embodiments of the regulator are particularly useful to effect long-term and high-speed pressure changes in high-resistance fluidic channel networks.

10 Claims, 12 Drawing Sheets

Related U.S. Application Data

(60) Provisional application No. 61/271,507, filed on Jul. 22, 2009.

(51) Int. Cl.
*G05B 15/02* (2006.01)
*B01L 3/00* (2006.01)

(52) U.S. Cl.
CPC ...... *B01L 3/50273* (2013.01); *G05D 16/2066* (2013.01); *G05D 16/2086* (2013.01); *Y10T 137/0396* (2015.04); *Y10T 137/7761* (2015.04); *Y10T 137/87249* (2015.04)

(58) Field of Classification Search
CPC ...... Y10T 137/87249; Y10T 137/7761; G01N 35/1095; B01L 3/50273
USPC ................ 137/12, 14, 487.5; 138/28, 30, 31
See application file for complete search history.

(56) References Cited

U.S. PATENT DOCUMENTS

| | | | |
|---|---|---|---|
| 5,158,230 | A | 10/1992 | Curran |
| 5,630,709 | A | 5/1997 | Bar-Cohen |
| 6,652,240 | B2 | 11/2003 | Wichert |
| 6,782,906 | B2 | 8/2004 | Chang |
| 9,170,267 | B2 * | 10/2015 | Kim ................... G01N 35/1095 |
| 2002/0008029 | A1 | 1/2002 | Williams et al. |
| 2002/0092564 | A1 | 7/2002 | Ollivier |
| 2002/0179445 | A1 | 12/2002 | Alajoki et al. |
| 2002/0187564 | A1 | 12/2002 | Chow et al. |
| 2003/0027225 | A1 | 2/2003 | Wada et al. |
| 2003/0041652 | A1 | 3/2003 | Spaid et al. |
| 2003/0051760 | A1 | 3/2003 | Johnson et al. |
| 2004/0178071 | A1 | 9/2004 | Harrison et al. |
| 2007/0134807 | A1 | 6/2007 | Bao et al. |
| 2008/0131323 | A1 | 6/2008 | Kuczenski et al. |

OTHER PUBLICATIONS

Non-final office action dated Oct. 30, 2012, issued in connection with related U.S. Appl. No. 12/841,743, filed Jul. 22, 2010.
Second Restriction Requirement dated Feb. 21, 2013, issued in connection with related U.S. Appl. No. 12/841,743, filed Jul. 22, 2010.
Final Office Action dated Apr. 3, 2013, issued in connection with related U.S. Appl. No. 12/841,743, filed Jul. 22, 2010.
Non-Final Office Action dated Apr. 7, 2014, issued in connection with related U.S. Appl. No. 12/841,743, filed Jul. 22, 2010.
Final Office Action dated Sep. 10, 2014, issued in connection with related U.S. Appl. No. 12/841,743, filed Jul. 22, 2010.
Non-Final Office Action dated Jan. 23, 2015, issued in connection with related U.S. Appl. No. 12/841,743, filed Jul. 22, 2010.
Notice of Allowance dated Jun. 19, 2015, issued in connection with related U.S. Appl. No. 12/841,743, filed Jul. 22, 2010.

\* cited by examiner

TABLE I

DESIGN PARAMETERS IN THE MECHANISM

| PARAMETERS | | VALUE (M) |
|---|---|---|
| $L_H$ | HORIZONTAL LINKAGE LENGTH | 0.126 |
| $L_V$ | VERTICAL LINKAGE LENGTH | 0.0508 |
| $C_X$ | X COORDINATE OF CENTER OF MOTOR SHAFT | 0.113 |
| $C_Y$ | Y COORDINATE OF CENTER OF MOTOR SHAFT | 0.0508 |
| r | RADIUS OF FLYWHEEL | 0.0127 |
| $L_P$ | DISTANCE FROM ORIGIN TO PINCH POINT | 0.0318 |
| $L_S$ | DISTANCE FROM ORIGIN TO SQUEEZE POINT | 0.0397 |
| $d_P$ | DIAMETER OF COMPLIANT NARROW TUBE | 0.000794 |
| $d_S$ | DIAMETER OF VARIABLE RESERVOIR | 0.00635 |
| $W_L$ | WIDTH OF LINKAGE | 0.0127 |

FIG. 5

TABLE II
DESIGN PARAMETERS AT A SET POINT ($\theta_0 = 125°$)

| PARAMETERS | | VALUE | UNIT |
|---|---|---|---|
| $P_r$ | UPSTREAM PRESSURE | 20.6 | kPa |
| $P_o$ | DOWNSTREAM PRESSURE | 19.6 | kPa |
| $R_r$ | UPSTREAM RESISTANCE | 5.1E+9 | Pa s/m³ |
| C | MICROCHANNEL CAPACITANCE | 4.0E-12 | m³/Pa |
| $R_i$ | MICROCHANNEL RESISTANCE | 1.1E+14 | Pa s/m³ |
| $u_P$ | SQUEEZE PUMP | 3.3E-7 | m³/Pa |
| $u_R$ | VARIABLE RESISTANCE | 5.6E+12 | Pa s/m³ |
| $\frac{du_P}{d\theta}$ | DERIVATIVE OF $u_P$ W.R.T. $\theta$ | -2.8E-9 | m³/deg |
| $\frac{du_R}{d\theta}$ | DERIVATIVE OF $u_R$ W.R.T. $\theta$ | -4.5E+12 | Pa s/m³ deg |

FIG. 9

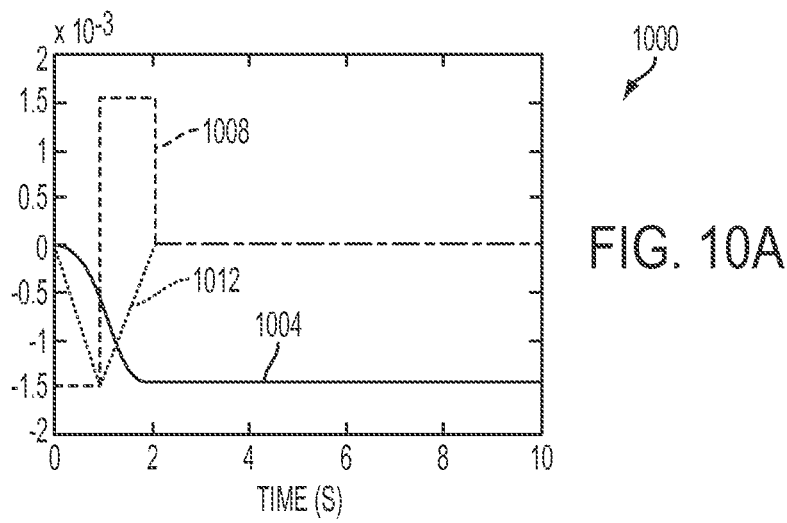

FIG. 10A

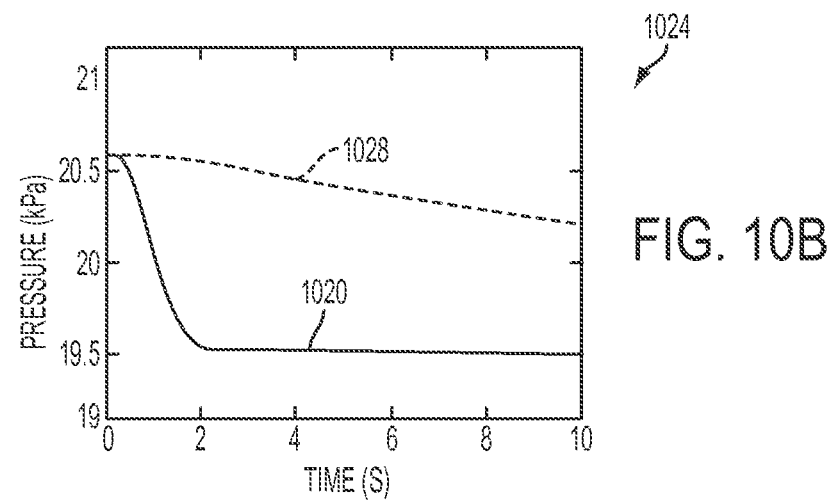

FIG. 10B

TABLE III
PHYSICAL PARAMETERS IN THE DC MOTOR AND THE MECHANISM

| PARAMETERS | | VALUE | UNIT |
|---|---|---|---|
| $J_m$ | MOMENT OF INERTIA OF ROTOR | 7.1E-6 | $kgm^2/s^2$ |
| $B_m$ | DAMPING RATIO | 3.5E-6 | Nms |
| $L_m$ | ELECTRIC INDUCTANCE | 5.1E-4 | H |
| $R_m$ | ELECTRIC RESISTANCE | 6.8E-1 | Ohm |
| $K_t$ | ELECTROMOTIVE FORCE CONSTANT | 1.7E-2 | Nm/Amp |
| $J_d$ | MOMENT OF INERTIA OF MECHANISM (EST.) | 3.0E-4 | $kgm^2/s^2$ |
| $B_d$ | DAMPING RATIO OF MECHANISM (EST.) | 1.0E-1 | Nms |
| $K_d$ | SPRING CONSTANT OF MECHANISM (EST.) | 1.0E+1 | N/m |

FIG. 11

FLUID-PRESSURE REGULATION SYSTEMS AND SOFTWARE

RELATED APPLICATION DATA

This application is a continuation of U.S. Nonprovisional patent application Ser. No. 12/841,743, filed Jul. 22, 2010, and titled "Fluid-Pressure Regulator and Related Methods and Systems", which application claims the benefit of priority of U.S. Provisional patent application Ser. No. 61/271,507, filed on Jul. 22, 2009, and titled "Apparatuses, Systems, And Methods Utilizing Laminar Flow Interface Control And For Controlling Laminar Flow Interface." Each of these applications is hereby incorporated by reference herein in its entirety.

STATEMENT REGARDING FEDERALLY SPONSORED RESEARCH AND DEVELOPMENT

This invention was made with partial government support under National Science Foundation grant number CMS-0555513. The U.S. government may have certain rights in this invention.

FIELD OF THE INVENTION

The present invention generally relates to the field of fluid systems. In particular, the present invention is directed to fluid-pressure regulation systems and software.

BACKGROUND

The study of the dynamics of cell processes is necessary for understanding cell function, organism development, and disease. Increasingly, control engineers and cell biologists are collaborating as they recognize similar attributes in the systems they study, such as amplification, positive and negative feedback, regulation and control, oscillatory and nonlinear behavior, bi-stable behavior, disturbance rejection, noise rejection, and robustness. In many instances, the vocabularies of the engineering and biology domains are the same with regard to dynamic systems. However, one significant difference between the two domains is that there is generally no separate control unit in a biological regulation process. Rather, feedback control of a reaction in a biochemical pathway is performed implicitly by biological agents downstream of the reaction which manipulate the activity of other biological agents upstream of the reaction.

Microfluidics techniques are ideally suited to creating and maintaining the types of external chemical gradients that generate the behavior just mentioned. The ability to determine the functioning of a single cell has been handicapped by the absence of technology to introduce spatiotemporal stimulation to localized subcellular domains within single cells of sub-micron specificity. Patch clamping, micropipetting, and laser microsurgery are useful for examining local domains, but none of these methods have the potential to be as robust as those enabled by a micro- and nano-technological approach. Alternative fabrication techniques at the organic-inorganic interface can regulate the attachment and spreading of individual cells, and fluidic devices have been implemented to mediate cell population attachment, as well as to deliver chemical reagents to specific cell populations. Many cellular characteristics and processes have been discovered to be spatially and temporally responsive, including cell structure, motility, and apoptosis. To measure internal cell responses, methods for working at subcellular levels with control over these gradient behaviors are needed. Micro- and nano-technological approaches are ideally suited to these applications, as they can be used to design and develop systems on the size scale of cells and molecules and have been successfully interfaced with the cellular and molecular worlds in areas such as DNA transport, drug delivery targeting for cancer treatments, and electrically stimulating neural cells.

In U.S. Patent Application Publication No. 2008/0131323, published on Jun. 5, 2008, and titled "Method and Apparatus Utilizing Laminar Flow Interface Control In A Microfluidic Device," the present inventors described the design, fabrication, testing, and operation of apparatuses, systems, and methods for controlling the position of the interface between two or more laminar flow streams in a microfluidic network. Those apparatuses, systems, and methods allow researchers to study the behavior of cells and other objects as "black box" systems, responding to input signals in observable ways to generate output signals that can include cell position or chemical concentration. For example, variations of a chemical or other environmental factor of a cell can constitute an "input," and the cell's response to these inputs can constitute an "output." The previous invention may be used to study fundamental dynamic responses of cells, including threshold response and frequency response.

In the '323 publication, control of the position of the interface between two or more laminar flow streams is achieved using a closed-loop system that regulates pressure instead of flow. That approach achieves a high precision of positioning of the interface even at very low flow rates of one or more streams. In one embodiment of the '323 publication, the pressure in the closed-loop system is controlled using a direct current motor to actuate a syringe plunger. While that embodiment achieves the goal of providing precise control over the interface between two or more laminar flow streams, it has a limitation in the relatively small volume of the syringes used in the pressure control system. An implication of this limitation is that it constrains the duration of studies that can be conducted with the system.

SUMMARY OF THE DISCLOSURE

In one implementation, the present disclosure is directed to a non-transitory machine-readable medium containing machine executable instructions for performing a method of controllably modulating pressure of a fluid at an inlet to a fluidic network or fluidic device using a variable-resistance variable-volume (VRVV) fluid-pressure regulator located upstream of the inlet of the fluidic network, wherein the VRVV fluid-pressure regulator includes a fluid path, a variable resistor located in the fluid path, and a variable-volume reservoir structure that includes a variable-volume reservoir in fluid communication with the fluid path downstream of the variable resistor and having a volume. The machine-executable instructions include a first set of machine-executable instructions for receiving a signal from a pressure sensor located downstream of the variable-volume reservoir; and a second set of machine-executable instructions for executing a pressure control algorithm designed and configured to generate, as a function of the signal, at least one control signal designed and configured for modulating pressure of the fluid at the inlet of the fluidic network or fluidic device by controlling the variable resistor to controllably change in a determined direction, either increasing or decreasing, resistance to flow of the fluid through the variable resistor along the flow path; and controlling the variable-volume reservoir structure to controllably change in the determined direction the volume of the variable-volume reservoir structure simultaneously with changing the resistance of the variable-volume resistor In another implementation, the present disclosure is directed to a system that includes a variable-resistance variable-volume (VRVV) fluid-pressure regulator designed and configured to be fluidly connected to an inlet of a fluidic network or fluidic device upstream of the fluidic network or fluidic device. The VRVV fluid-pressure regulator includes a fluid path; a variable resistor located in the fluid path; a variable-volume reservoir structure that includes a variable-volume reservoir in fluid communication with the fluid path downstream of the variable resistor and having a volume; a controller in operative communication with the variable resistor and the variable-volume reservoir structure and including: a microprocessor and a memory in operative communication with the microprocessor to allow the microprocessor to execute machine-executable instructions stored in the memory. The memory includes a first set of machine-executable instructions for receiving a signal from a pressure sensor located downstream of the variable-volume reservoir and a second set of machine-executable instructions for executing a pressure control algorithm designed and configured to generate, as a function of the signal, at least one control signal designed and configured for modulating pressure of the fluid at the inlet of the fluidic network or fluidic device by controlling, via the controller, the variable resistor to controllably change in a determined direction, either increasing or decreasing, resistance to flow of the fluid through the variable resistor along the flow path; and controlling, via the controller, the variable-volume reservoir structure to controllably change in the determined direction the volume of the variable-volume reservoir structure simultaneously with changing the resistance of the variable-volume resistor.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 5 is a table of design parameters of the VRVV modulator of FIGS. 3A-B;

FIG. 9 is a table of design parameters at a set point of the motor angle being 125°;

FIG. 10A is a graph of angular acceleration, angular velocity and angular position versus time for an exemplary input signal input into the motor of the VRVV modulator of FIGS. 3A-B;

FIG. 10B is a graph of pressure versus time illustrating the difference in response between a scenario in which variable resistance and variable volume of the VRVV modulator of FIGS. 3A-B are coupled and a scenario in which variable resistance was used alone;

FIG. 11 is a table of physical parameters of the DC motor and other components of one example of the VRVV modulator of FIGS. 3A-B;

DETAILED DESCRIPTION

Figure 1:
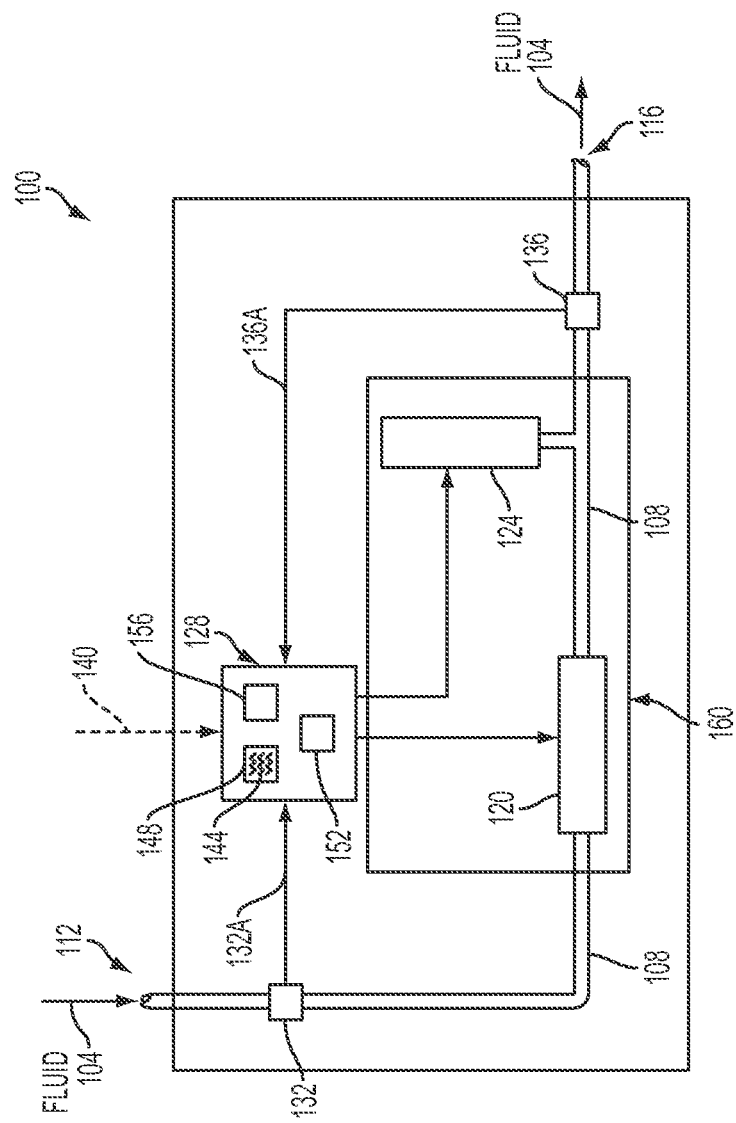
FIG. 1 is a schematic diagram of a variable-resistance variable-volume (VRVV) fluid-pressure regulator of the present invention.

Referring now to the drawings, FIG. 1 shows a variable-resistance variable-volume (VRVV) fluid-pressure regulator 100 illustrating one embodiment of the present invention. As described below in detail, features of a VRVV fluid-pressure regulator of the present disclosure, such as VRVV fluid-pressure regulator 100 of FIG. 1, include the fast control of the pressure of a fluid 104 output by the regulator and the ability to provide a relatively large volume of fluid at a precisely controlled pressure. These features are especially useful in biological microfluidic systems, such as the microfluidic systems disclosed in U.S. Patent Application Publication No. 2008/0131323, published on Jun. 5, 2008, and titled "Method and Apparatus Utilizing Laminar Flow Interface Control In A Microfluidic Device" (hereinafter "the '323 publication"), which is hereby incorporated by reference herein for its teachings of microfluidic devices, systems, methods, and background information that are commensurate with the present disclosure. In the embodiments disclosed herein, fluid 104 is essentially incompressible under conditions at which such embodiments would typically be implemented.

As described in the Background section above, one embodiment disclosed in the '323 publication involves the precise controlling of pressure input into a microfluidic device using syringes, which have relatively small volumes. While the syringe-based pressure regulation of the '323 publication provides excellent results, experiments can be limited by the relatively small volumes of the syringes used.

A VRVV fluid-pressure regulator of the present disclosure does not have such a limitation. Prior to describing an exemplary embodiment of a microfluidic system of the present invention, basic features of VRVV fluid-pressure regulator 100 are first described.

Referring still to FIG. 1, VRVV fluid-pressure regulator 100 includes a conduit 108 for conveying fluid 104 from an inlet 112 of the regulator to an outlet 116 of the regulator. During operation of VRVV fluid-pressure regulator 100, inlet 112 is fluidly connected to a suitable source (not shown) of fluid 104, such as a pressurized or non-pressurized reservoir. Similarly, during operation of VRVV fluid-pressure regulator 100, outlet 116 is typically connected to an inlet of a fluidic system or device (not shown), such as a microfluidic device, for which it is desired/necessary to regulate the pressure and/or other characteristics of the fluid flow entering the system or device. Those skilled in the art will readily understand the variety of fluid sources and fluidic systems/devices to which VRVV fluid-pressure regulator 100 can be fluidly connected. Conduit 108 can be any suitable continuous or segmented conduit, such as flexible-wall conduits (tubing, hosing, piping, etc.), rigid-wall conduit (tubing, hosing, piping, etc.), and any combination thereof, as needed to suit a particular application of VRVV fluid-pressure regulator.

VRVV fluid-pressure regulator 100 includes a fluid-type variable resistor 120, a variable-volume reservoir 124, and a controller 128 that precisely controls the resistance of the resistor and the volume of the variable-volume reservoir in concert and simultaneously with one another to regulate the pressure of fluid 104 at outlet 116. Variable resistor 120 is located in fluid series with conduit 108 and can include any one or more of a variety of flow elements having a fluid resistance that can be changed under control, for example, using a suitable actuator (not shown). In one example, variable resistor 120 is a flexible-walled tube, or a section of such tube when that tube forms conduit 108 or a portion thereof. In this example, the variable resistance is provided by changing the amount that the tube is pinched, squeezed, or otherwise laterally compressed. An important feature of this compressed-tube arrangement for variable resistor 120 is that laminar flow of fluid 104 can be maintained within conduit 108 from inlet 112 to outlet 116. Laminar flow is needed in many applications in which VRVV fluid-pressure regulator 100 can be used, such as microfluidic device applications. As those skilled in the art will appreciate, another type of variable resistor can be used in place of a pinched tube, such as a valve or other fluid element that controllably constricts the flow of fluid 104. Whatever type of resistor is selected, this resistor will need to be controlled in conjunction with the variable-volume element, for example, by mechanically tying the two together.

Variable-volume reservoir 124 is located in fluid series with conduit 108 and variable resistor 120 and downstream of the resistor. Variable-volume reservoir 124 can include any one or more of a variety of fluid elements that can contain a volume of fluid 104 that can be changed under control, for example, using a suitable actuator (not shown). In one embodiment, variable-volume reservoir 124 includes a section of flexible-wall tube in fluid communication with conduit 108. In this embodiment, the variable volume is provided by changing the amount that the tube is squeezed or otherwise compressed to change the volume of the tube. In one example of this embodiment, the tubing used for variable-volume reservoir 124 is larger in diameter than the tubing used for conduit 108 and variable resistor 120. In another embodiment, variable-volume reservoir 124 is a rigid-wall closed reservoir (not shown) partially filled with a second fluid that is kept separate from fluid 104. Those skilled in the art will understand how to implement these and other variations of variable-volume reservoir 124 such that further explanation is not necessary for those skilled in the art to implement the present invention to its broadest scope.

Controller 128 controls the resistance of variable resistor 120 and the volume of variable-volume reservoir 124 via one or more suitable actuators and/or other device(s) that interact with the variable resistor and the variable-volume reservoir to change their respective resistance and volume. Controller 128 will typically base the control of variable resistor 120 and variable-volume reservoir 124 on one or more inputs from, for example, one or more corresponding pressure sensors. In the embodiment shown, controller 128 utilizes inputs 132A, 136A from corresponding respective pressure sensors 132, 136. Pressure sensor 132 senses the pressure in fluid 104 upstream of variable resistor 120, while pressure sensor 136 senses the pressure in fluid 104 downstream of variable-volume reservoir 124. Depending on the application, controller 128 may also use information collected via one or more other inputs, such as input 140, which may also provide pressure and/or flow information from one or more locations outside of VRVV fluid-pressure regulator 100. An example of such additional input is seen in the fluidic system example of FIG. 2, wherein the pressure of a second fluid is measured for use in controlling the fluid flow of the first fluid (which is equivalent to fluid 104 in the embodiment of FIG. 1) in order to ultimately control the joining of the flows in a microfluidic device.

Based on the inputs, here, provided by pressure sensors 132, 136, controller 128 executes a control algorithm, which in this embodiment is implemented in machine-executable instructions 144 stored in a memory or other machine-readable medium 148 associated with the controller that stores the instructions in a non-transitory manner. Controller 128 can include one or more processors, here single processor 152, to execute instructions 144. Processor 152 can be any of a variety of devices, such as an application-specific integrated circuit, a component of a system-on-chip, or a general-purpose processor, among others.

As those skilled in the art will readily understand, controller 128 can also include, as necessary, other components necessary to provide a fully functioning controller. Such other components can include analog-to-digital converters, digital-to-analog converters, and one or more transceivers. Controller 128 may also provide one or more interfaces, such as a graphical user (GUI) interface 156, that allows a user and/or an overall system program to, for example, control parameters of the control algorithm. Those skilled in the art will readily understand how to select and implement the components and interface(s) for a particular application such that further description thereof is not necessary for those skilled in the art to implement the present invention to its fullest scope. In some alternative embodiments, controller 128 could be implemented using hardwired logic circuitry.

Without presenting the detailed specifics of a particular example, the control algorithm of controller 128 controls variable resistor 120 and variable-volume reservoir 124 as follows. When it is desired to increase the pressure in fluid 104 at outlet 116 of VRVV fluid-pressure regulator 100, controller 128 controls variable resistor 120 in a manner that decreases the resistance across the variable resistor. At the same time, controller 128 controls variable-volume reservoir 124 in a manner that decreases the volume of the variable-volume reservoir. Conversely, when it is desired to decrease the pressure in fluid 104 at outlet 116 of VRVV fluid-pressure regulator 100, controller 128 controls variable resistor 120 in a manner that increases the resistance across the variable resistor, while at the same time the controller controls variable-volume reservoir 124 in a manner that increases the volume of the variable-volume reservoir. In many applications, the presence of variable-volume reservoir 124 allows VRVV fluid-pressure regulator 100 to be more responsive than a regulator having only a variable resistor. For example, when effecting a decrease in pressure at outlet 116 when the outlet of VRVV fluid-pressure regulator 100 fluidly coupled to a high fluid-resistance fluidic network (not shown), such as a microfluidic channel network, the pressure drop is quicker when variable-volume reservoir 124 is present. The pressure change would take longer because the pressure at outlet 116 would not drop until fluid 104 drained from the fluidic network. For convenience, the combination of variable resistor 120 and variable-volume reservoir 124 in series with one another in a fluid system is referred to as an "VRVV modulator" and is indicated by numeral 160 in FIG. 1.

Figure 2:
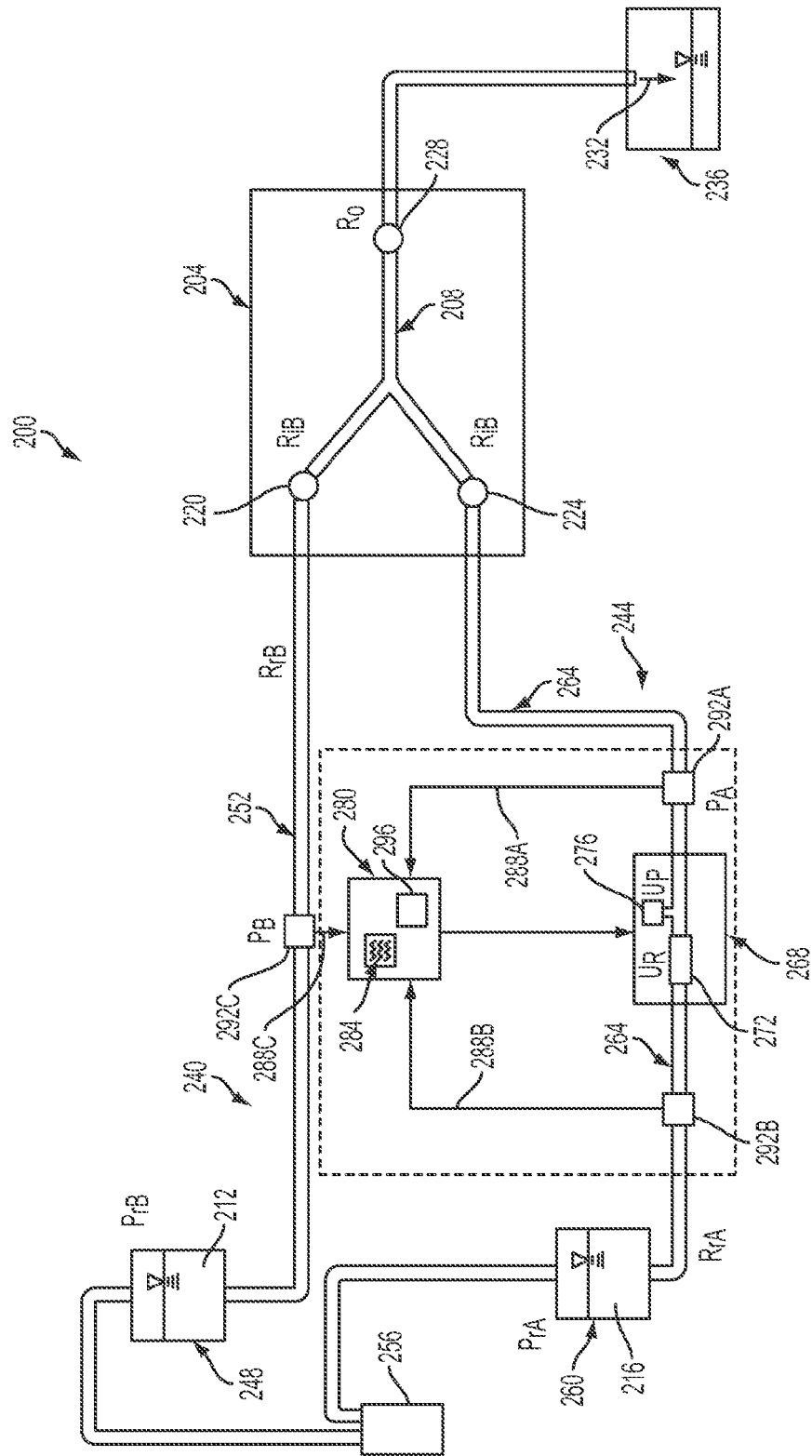
FIG. 2 is a schematic diagram of a microfluidic system of the present invention that includes a VRVV fluid-pressure regulator.

FIG. 2 illustrates a microfluidic system 200 of the present invention that includes a microfluidic device 204 having a Y-shaped microchannel network 208 for flowing first and second fluids 212, 216 adjacent one another in a common channel in a laminar fashion. As described in the '323 publication, such a microchannel network and similar microchannel networks are useful not only for controlling a chemical environment of a biological cell, but also for use in other technologies and applications, such as the manufacture and operation of microdevices, microsystems, and micro-electromechanical systems, semiconductor fabrication, and molecular self-assembly, among others. Those skilled in the art will readily appreciate that microchannel network 208 shown is merely exemplary. Examples of other microchannel devices suitable for use in microfluidic system 200 or a modified version of microfluidic system 200 include the microchannel devices disclosed in the '323 publication in FIGS. 4-12 and corresponding respective accompanying descriptions, all of which are hereby incorporated by reference herein.

In addition, FIGS. 1-3, 13, and 14 of the '323 publication and the corresponding respective accompanying descriptions, all of which are hereby incorporated by reference herein, describe a Y-shaped microchannel network and its functioning in detail. Moreover, various portions of FIGS. 15-29 of the '323 publication and the corresponding respective accompanying descriptions, all of which are hereby incorporated by reference herein, are directed to the operation and use of microchannel networks and provide specific examples of using such networks. Included in the incorporated material from the '323 publication are the explanations of laminar fluid flow and how side-by-side laminar flow is achieved in microchannel networks. Consequently, the reader should consult those parts of the '323 publication for further details of microchannel network 208 of the present disclosure, its operation and use and the operation and use of other microchannel networks if the reader is interested in learning more about such networks and their operation and uses.

With continuing reference to FIG. 2 of the present disclosure, exemplary microchannel network 208 has two inlets, i.e., first and second inlets 220, 224, for receiving corresponding respective fluids 212, 216 and an outlet 228 for outputting a waste stream 232 from the network. In this embodiment, outlet 228 outputs waste stream 232 to a waste reservoir 236. On the input side of microchannel network 208, microfluidic system 200 has two fluid-delivery systems, specifically, a first fluid-delivery system 240 that delivers first fluid 212 to first inlet 220 of the microchannel network and a second fluid-delivery system 244 that delivers second fluid 216 to second inlet 224 of the microchannel network. In this example, first fluid-delivery system 240 is a fixed-pressure system that delivers first fluid 212 to first inlet 220 at a constant pressure, and second fluid-delivery system 244 is a variable-pressure system that delivers second fluid 216 to second inlet 224 and allows a user to control the delivery pressure in order to adjust the location of the laminar flow interface (not shown, but see, e.g., FIGS. 3, 6, 8, 9-13, 19-22, 25 and 26 of the '323 publication which are hereby incorporated by reference).

In the embodiment shown, first fluid-delivery system 244 includes a pressurized first reservoir 248 and a conduit 252 that fluidly couples the first reservoir to first inlet 220 of microchannel network 208. First reservoir 248 contains first fluid 212 and is pressurized in this example using pressurized gas, here, from a nitrogen pressure tank 256. Similarly, second fluid-delivery system 244 includes a pressurized second reservoir 260 and a conduit 264 that fluidly couples the second reservoir to second inlet 224 of microchannel network 208. Second reservoir 260 contains second fluid 216 and is pressurized using the same nitrogen pressure tank 256 that pressurizes first reservoir 248.

Second fluid-delivery system 244 includes a VRVV modulator 268, which, like VRVV modulator 160 of FIG. 1, includes a fluid-type variable resistor 272 and a fluid-type variable-volume reservoir 276 fluidly coupled within conduit 264 in series with one another. VRVV modulator 268 of FIG. 2 works in the same way as VRVV modulator 160 of FIG. 1. That is, the pressure is increased at second inlet 224 of microchannel network 208 by decreasing both the resistance of variable resistor 272 and the volume of variable-volume reservoir 276 in concert with one another. Conversely, the pressure is decreased at second inlet 224 of microchannel network 208 by increasing both the resistance of variable resistor 272 and the volume of variable-volume reservoir 276 in concert with one another. It is noted that the forms of variable resistor 272, variable-volume reservoir 276, and more generally VRVV modulator 268 can be any of the forms described above relative to the like elements of FIG. 1 or described below relative to the like elements of FIG. 3.

Microfluidic system 200 also includes a controller 280, which can be the same as or similar to controller 128 of FIG. 1. In this example, controller 280 executes a control algorithm 284 that controls the resistance of variable resistor 272 and the capacitance of variable-volume reservoir 276 as a function of pressure signals 288A-C from corresponding respective pressure sensors 292A-C to control the pressure at second inlet 224 of microchannel network 208. As seen in FIG. 2, pressure sensor 292A is located downstream of VRVV modulator 268 between the VRVV modulator and second inlet 224 of microchannel network 208 and effectively monitors the pressure of second fluid 216 at the second inlet. Pressure sensor 292B is located upstream of VRVV modulator 268 between second pressurized reservoir 260 and the VRVV modulator and effectively monitors the pressure of second fluid 216 at the inlet of the VRVV modulator. Pressure sensor 292C is located between first reservoir 248 and first inlet 220 to microchannel network 208 and effectively monitors the pressure of first fluid 212 at the first inlet of the microchannel network.

With the pressure of first fluid 212 fixed, by controller 280 being able to change the pressure of second fluid 216 it is possible to adjust the location of the laminar-flow interface (not shown, but see, e.g., FIGS. 13, 19, 21, 22, 25, and 26 of the '323 publication, which are hereby incorporated by reference herein) between the first and second fluids at the junction 208A of fluid network. As described in the '323 publication, information on the current location of laminar-flow interface can be used in a feedback control scheme that can be part of control algorithm 284. Such feedback information can be provided by a user that visually observes the location of the laminar-flow interface and uses those observations to adjust the pressure of second fluid 216 at second inlet 224, for example via an appropriate user interface 296. The '323 publication describes examples of such an interface relative to interfaces 34, 36 thereof, and that disclosure is hereby incorporated by reference herein. In alternative embodiments, the feedback information on the current location of the laminar-flow interface between first and second fluids 212, 216 can be obtained automatedly, for example, using a image-processing system (not shown). Such image-processing systems are shown and described in the '323 publication in FIGS. 15-18 and accompanying descriptions, which are hereby incorporated by reference herein for their disclosure of same.

As those skilled in the art will readily appreciate, microfluidic system 200 is merely exemplary of a variety of microfluidic systems that can utilize a VRVV modulator and/or VRVV fluid-pressure regulator of the present disclosure. Indeed, skilled artisans having read the '323 publication will recognize that a VRVV fluid-delivery system, such as second fluid-delivery system 244 of FIG. 2 of the current disclosure, can be substituted for any one or more of the "pressure controllers" of the '323 publication, such as pressure controllers 12, 14 of FIGS. 1, 15-17, 19, 28 and 29 and pressure controller 142 of FIG. 29. Therefore, all of those figures and accompanying descriptions thereof are hereby incorporated by reference herein for their teachings of applications in which a VRVV fluid-delivery system of the present disclosure can be used.

Exemplary VRVV Modulator

Figure 3A:
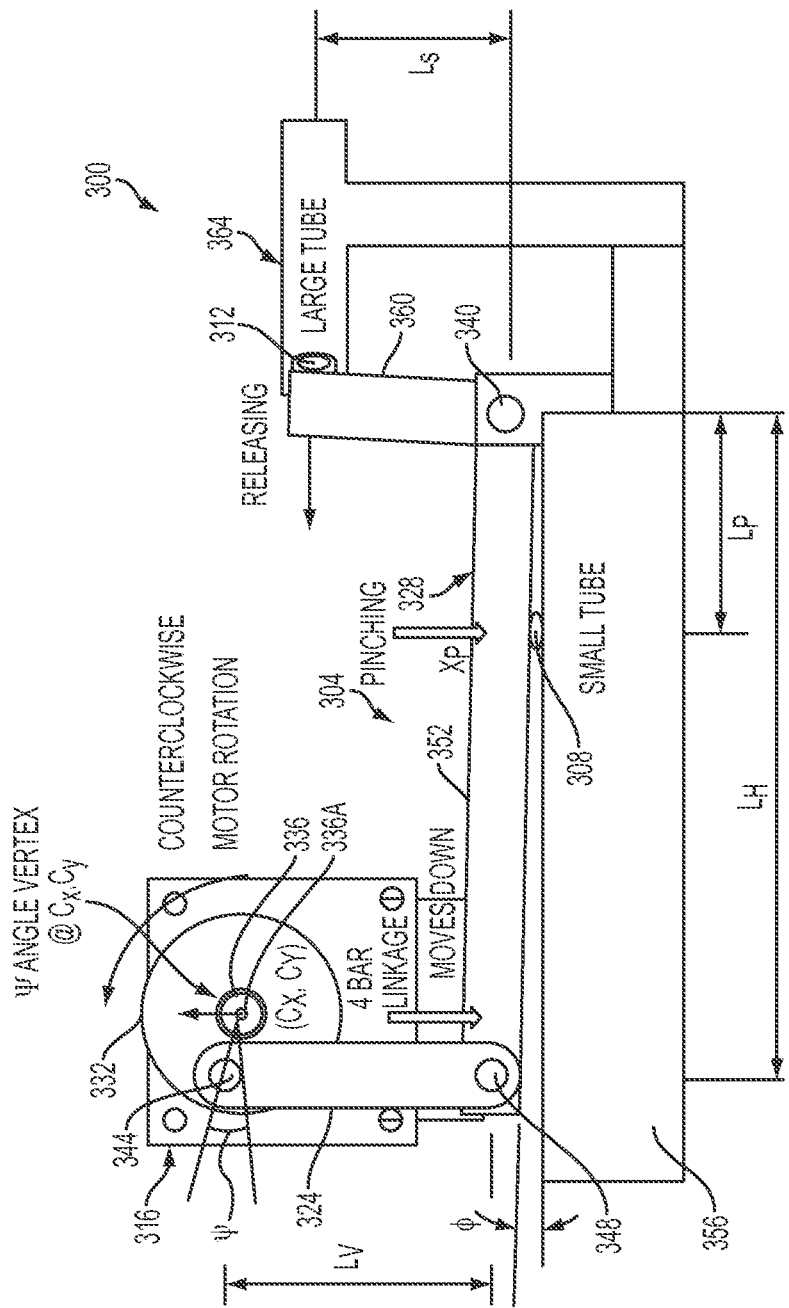
FIGS. 3A-B are diagrams of an integral VRVV modulator of the present invention that can be used in each of the fluid-pressure regulator of FIG. 1 and the microfluidic system of FIG. 2, illustrating the modulator, respectively, in a pressure-decreasing state and a pressure-increasing state.
Figure 3B:
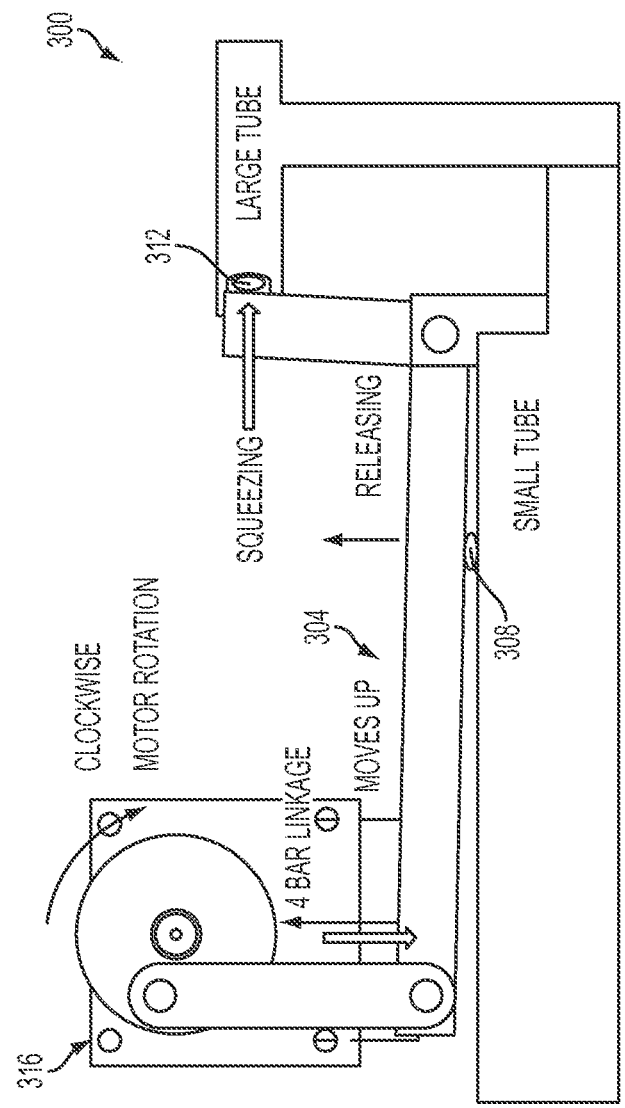

FIGS. 3A-B show an exemplary VRVV modulator 300 that can be implemented, for example, as VRVV modulator 268 in microfluidic system 200 of FIG. 2. As seen in FIG. 3A, VRVV modulator 300 utilizes a multi-link mechanism 304 for simultaneously acting on a first compliant-walled tube 308 (which corresponds to variable resistors 120 and 272 of FIGS. 1 and 2, respectively) and a second compliant-walled tube 312 (which corresponds to variable-volume reservoirs 124 and 276 of FIGS. 1 and 2, respectively) using a single actuator, here a direct-current (DC) motor 316. FIG. 3A illustrates motor 316 actuating multi-link mechanism 304 in a manner that simultaneously pinches first tube 308 and releases a squeeze on second tube 312. Such actuation is used when it is desired to lower the pressure at the outlet (not shown, but corresponds to outlet 116 of VRVV modulator 160 of FIG. 1) of VRVV modulator 300. In the manner described above, by pinching or constricting first tube 308, the pressure at the outlet begins to decrease as a function of the pressure downstream of the outlet. If the downstream pressure takes time to dissipate because of the downstream conditions, such as a slow-draining fluidic network, the simultaneous release of the squeeze on second tube 312 acts to dissipate that pressure as the volume within the second tube increases.

Conversely, FIG. 3B illustrates motor 316 actuating multi-link mechanism 304 in a manner that simultaneously releases a pinch on first tube 308 and squeezes second tube 312. Such actuation is used when it is desired to raise the pressure at the outlet of VRVV modulator 300. By releasing the pinch on first tube 308, the pressure at the outlet increases. The simultaneous squeezing of second tube 312, which reduces the volume of the second tube, also acts to increase the pressure at the outlet. In this example, in their relaxed states both first and second tubes have circular cross-sectional shapes and the first tube has a smaller diameter than the second tube. Further details of the working of VRVV modulator 300 are described in sections below.

Referring again to FIG. 3A, multi-link mechanism 304 includes a first linkage 324, here a straight bar, a second linkage 328, here an L-shaped bar, and a flywheel 332 fixedly mounted to a central rotational shaft 336 of motor 316, which rotates about a rotational axis 336A. Second linkage 328 is pivotably secured to a fixed pivot 340, and first linkage 324 is pivotably attached to flywheel 332 and second linkage 328 via corresponding respective pivot pins 344, 348. When pinched by multi-link mechanism 304, first tube 308 is pinched between lower leg 352 of second linkage 328 and a base 356 that is fixed relative to motor 316. When multi-link mechanism 304 squeezes second tube 312, the second tube is squeezed between upper leg 360 of second linkage 328 and a resisting member 364 that is fixed relative to base 356 and motor 316.

Model of the VRVV Modulator

Referring to FIG. 2 and also to FIGS. 3A-B and 4A-B, FIG. 4A is a circuit representation 400 of microfluidic system 200 of FIG. 2 in which VRVV modulator 300 of FIGS. 3A-B is used for VRVV modulator 268 of FIG. 2. This representation uses the following nomenclature: fluidic resistance is denoted R, fluidic capacitance is denoted C, variable fluidic resistance is denoted $U_R$, and a "squeeze pump" (i.e., the change in volume over time of variable-volume reservoir 276 of FIG. 2 (and second tube 312 of FIGS. 3A-B) is denoted $U_P$. The diamond symbol 404 is a dependent current source, $P_r$ is the upstream pressure in pressure tank 256, $R_r$ represents the constant flow resistance between the upstream and the downstream, P represents the downstream pressure that is desired to be regulated, $R_i$ represents the fluidic resistance of an inlet 220, 224 of microfluidic channel network 208, and $R_o$ is the fluidic resistance of outlet 228 of the network. The subscripts A and B indicate the two different branches leading, respectively, to second and first inlets 224, 220 of microfluidic network 208.

Figure 4A:
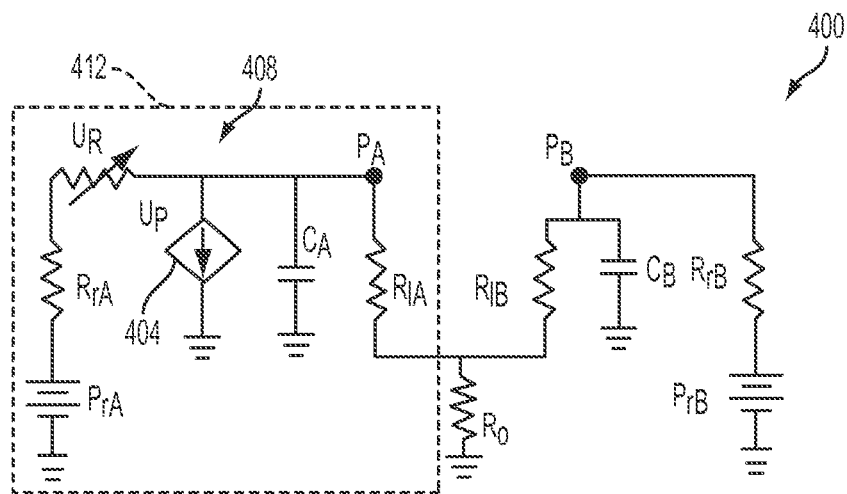
FIG. 4A is a circuit representation for the microfluidic system of FIG. 2 implementing the VRVV modulator of FIGS. 3A-B.
Figure 4B:
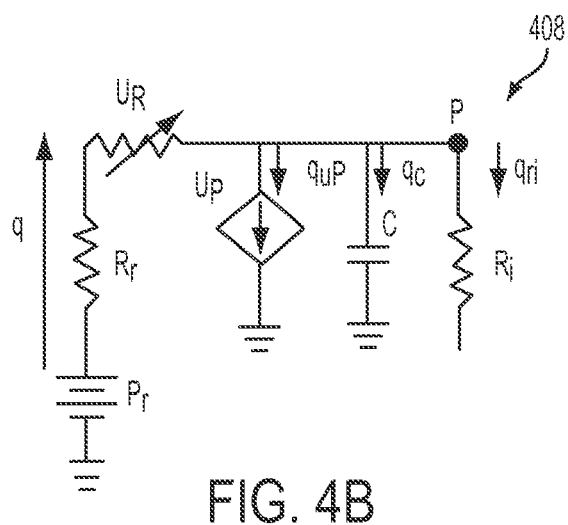
FIG. 4B is a portion of the circuit expression of FIG. 4A that represents the second fluid-delivery system of the microfluidic system of FIG. 2, showing the flow rates in the regulating streams.

Under the assumption that $R_i \gg R_o$, the inlet branches of microfluidic network 208 are decoupled, allowing separate analysis of the portion 408 of fluidic-circuit representation 400 indicated by a dashed line 412 in FIG. 4A and that corresponds to second fluid-delivery system 244 of FIG. 2. FIG. 4B is an enlargement of portion 408 of FIG. 4A inside dashed rectangle 412. For convenience, the subscripts A and B have been suppressed. To derive a dynamic model, the total flow rate, q, out of the reservoir is considered thusly:

$$q = q_{R_i} + q_{u_p} + q_C \quad \text{Eq. (1)}$$

Equations (2) and (3) below express two of the flows in terms of pressure difference and resistance:

$$q = \frac{P_r - P}{R_r + u_R} \quad \text{Eq. (2)}$$

$$q_{R_i} = \frac{P}{R_i} \quad \text{Eq. (3)}$$

Equation (4) below shows the flow in terms of the squeeze pump using variable-volume reservoir 276 and a capacitance in the network:

$$q_{u_P} + q_C = \frac{dV_g}{dt} + C\frac{dP}{dt} \qquad \text{Eq. (4)}$$

wherein Vg is the volume of the fluidic network when the inlet pressure is equal to atmosphere pressure. Note that $V_g = \int u_p dt + V_{gtubing}$ where $V_{gtubing}$=constant is the volume of the portions of conduit 264 of microfluidic network 208 outside of variable-volume second tube 312 that is squeezed by pumping. In this model, it is assumed that the capacitance of microfluidic network 208 is constant, i.e.

$$\frac{dC}{dt} = 0.$$

Substituting Equations (2)-(4) into Equation (1) gives the dynamic pressure model of Equation (5) as follows:

$$\frac{dP}{dt} = -\left(\frac{1}{R_iC} + \frac{1}{(R_r + u_R)C}\right)P + \frac{P_r}{(R_r + u_R)C} - \frac{1}{C}\frac{dV_g}{dt} \qquad \text{Eq. (5)}$$

Multi-Link Mechanism Design

As described above in connection with FIGS. 3A-B, exemplary VRVV modulator 300, which includes DC motor 316 with flywheel 332 and first and second linkages 324, 328 for pinching compliant narrow first tube 308 through the main fluid network and squeezing a variable-volume second tube 312 as a branch connected to the main stream. For a decrease in pressure at the outlet of VRVV modulator 300, shaft 336 of motor 316 rotates counter clockwise (FIG. 3A), then lower leg 352 of second linkage 328 moves down and upper leg 360 of the second linkage moves left, thus pinching narrow first tube 308 to increase fluidic resistance and releasing variable-volume second tube 312 to increase the volume in the network. For an increase in pressure at the outlet of VRVV modulator 300, shaft 336 of motor 316 rotates clockwise (FIG. 3B), and lower leg 352 of second linkage 328 moves up and upper leg 360 of the second linkage moves right, releasing narrow first tube 308 to decrease fluidic resistance and squeezing variable-volume second tube 312 to decrease the volume in the network. Therefore, the downstream pressure at second inlet 224 to microfluidic channel network 208 (essentially the pressure at the outlet of VRVV modulator 300 of FIGS. 3A-B) can be regulated through this mechanism.

The pinch and squeeze displacements of tubes 308, 312 are represented as a function of the angle of motor 316 from the geometric relations shown in FIG. 3A. Rotational axis 336A of motor shaft 336 is ($C_x$, $C_y$) relative to origin (0,0) which is at rotational axis of fixed pivot 340 of second linkage 328. The geometric relationship between components of VRVV modulator 300 as shown in FIG. 3A is given in (6) as follows:

$$\{L_H \cos\phi - (r\cos\psi + C_x)\}^2 + \{(r\sin\psi + C_y) - L_H\sin\phi\}^2 = L_V^2 \qquad \text{Eq.(6)}$$

In the present example, the motor angle $\theta$ is 5.9 times as large as the flywheel rotation angle $\psi$ due to the gear ratio of the motor angle. The sizes of narrow first tube 308 and variable-volume second tube 312 limit the range of the link angle. From Table 1 of FIG. 5, the link angle $\phi$ for this small range is approximately linear and given by:

$$\phi = 0.0135\theta + 0.3$$

where $$\phi_{min} = 1.947° \ (\theta = 122°)$$

$$\phi_{max} = 3.365° \ (\theta = 227°) \qquad \text{Eq.(7)}$$

where $\phi_{min}$=1.947° ($\theta$=122°), $\phi_{max}$=3.365° ($\theta$=227°). Also, the actual amounts of the pinch $X_P$ and the squeeze $X_S$ are given as a function of the motor angle $\theta$ by Equations (8) and (9), below. The ranges of the pinch and squeeze can be controlled in VRVV modulator 300 by modulating $L_P$ and $L_S$ (FIG. 3A), which are the locations of compliant narrow first tube 308 and of variable-volume second tube 312 from the origin.

$$X_P = L_P(\tan\phi_{max} - \tan\phi) = 0.0318 \cdot (0.0588 - \tan(0.0135 \cdot \theta + 0.3)) \qquad \text{Eq.(8)}$$

$$X_S = L_S(\tan\phi - \tan\phi_{min}) = 0.0394 \cdot (\tan(0.0135 \cdot \theta + 0.3) - 0.0339) \qquad \text{Eq.(9)}$$

Figure 6:
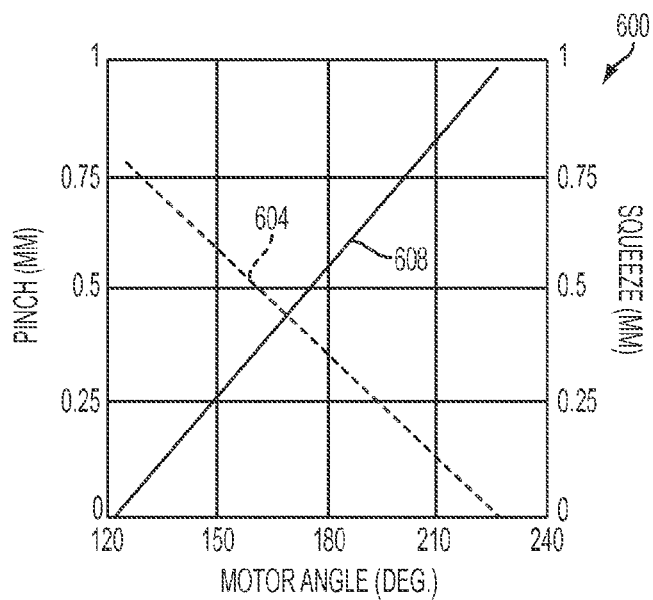
FIG. 6 is a graph of pinch and squeeze of the narrow tube and the variable-volume tube, respectively, versus motor angle for one example of the VRVV modulator of FIGS. 3A-B.

FIG. 6 is a graph 600 showing the pinch (dashed line 604) of narrow first tube 308 and the squeeze (solid line 608) of variable-volume second tube 312 with respect to the motor angle $\theta$ by Equations (8) and (9). These parameters are actually nonlinear with respect to the motor angle, but can be approximated as linear in the small operating range of the link angle. To enable both squeeze and release mechanism at the initial operating point, a preload was applied to variable-volume second tube 312 by tuning $L_P$ and $L_S$, which also prevents the fluidic resistance from being infinite at the initial link angle due to a complete pinching of narrow first tube 308.

Figure 7:
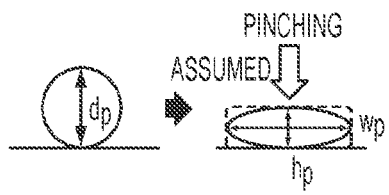
FIG. 7 is a diagram depicting an approximation technique for determining the cross-sectional area of the tubes of the VRVV modulator when pinched.

When narrow first tube 308 is pinched, its deformation is nonlinear. It is difficult to determine the actual deformation in tubes 308, 312 due to pinching and squeezing. In this example, it is assumed that the inner circumference of each tube 308, 312 is constant when the tube is pinched and that the shape of the inner tube can be approximated by a rectangular cross section, as illustrated in FIG. 7. With this approximation, the inner height $h_p$ of pinched narrow first tube 308 by subtracting the pinched length $X_p$ from the tube diameter $d_p$ using Equation (10), below, and its inner width $w_p$ by the assumption of a constant inner circumference using Equation (11), below. In the same manner, the inner height $h_p$ of the squeezed variable-volume second tube 312 can be determined by subtracting the squeezed length $X_S$ from the original inner height using Equation (12), below, and its inner width $w_p$ by the same assumption using Equation (13), below.

$$h_P(\theta) = d_P - X_P(\theta) \qquad \text{Eq. (10)}$$

$$w_P(\theta) = \frac{\pi}{2}d_P - h_P(\theta) \qquad \text{Eq. (11)}$$

$$h_S(\theta) = L_S(\tan\phi_{max} - \tan\phi) = 0.0394 \cdot (0.0588 - \tan(0.0135 \cdot \theta + 0.3)) \qquad \text{Eq. (12)}$$

$$w_S(\theta) = \frac{\pi}{2}d_S - h_S(\theta) \qquad \text{Eq. (13)}$$

Using the assumption of the tube geometry of FIG. 7, the variable fluidic resistance can be approximately computed using the inner height $h_p$ and width $w_p$ from Equations (10)

and (11). Equation (14), below, is an approximate form of the fluidic resistance formula when the width $w_p$ is much larger than the height $h_p$.

$$u_R(\theta) \approx \frac{12 \mu L}{w_p(\theta)(h_p(\theta))^3} \qquad \text{Eq. (14)}$$

Figure 8:
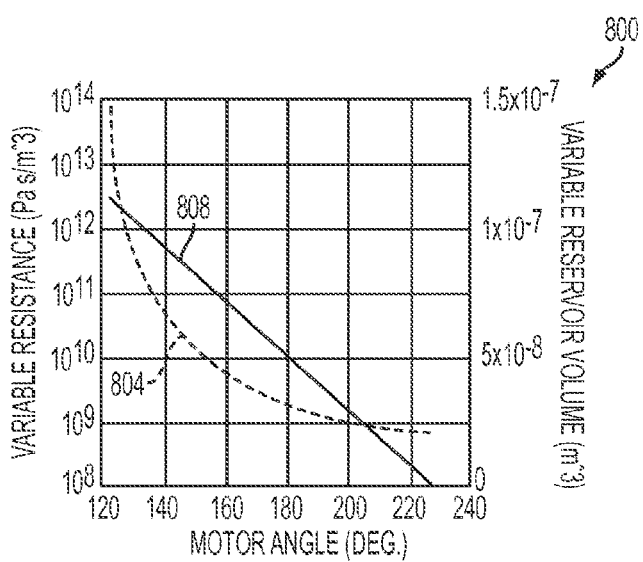
FIG. 8 is a graph of variable resistance and variable volume versus motor angle for one example of the VRVV modulator of FIGS. 3A-B.

The volume of variable-volume second tube 312 for pumping with respect to the motor angle $\theta$ is:

$$\int u_p(\theta) dt \approx w_L \cdot w_S(\theta) \cdot h_S(\theta) \qquad \text{Eq. (15)}$$

where $w_L$, is the width of linkage jaw 378, $h_S$ is the height (separation between the jaws) of variable-volume second tube 312 that forms the squeeze pump, and $d_S$ is the diameter of the variable-volume tube. FIG. 8 is a graph 800 showing the fluid resistance (dashed line 804) of narrow first tube 308 and the variable volume (solid line 808) of variable-volume second tube 312 with respect to the motor angle $\theta$ by Equations (14) and (15).

Linearization

In this example, microfluidic system 200 (FIG. 2) operates in the vicinity of a set point where the dynamics can be approximated as linear given by the vector matrix form of the following Equations (16) and (17) for a state vector $\vec{x}$ and a scalar input u:

$$\frac{d\vec{x}}{dt} = A\vec{x} + Bu \qquad \text{Eq. (16)}$$

$$\vec{y} = C\vec{x} + Du \qquad \text{Eq. (17)}$$

where A, B, C, and D are matrices. Equation (18) gives the following definition of the state vector and the input scalar:

$$\vec{x} = \begin{bmatrix} x_1 \\ x_2 \end{bmatrix} = \begin{bmatrix} P \\ \theta \end{bmatrix} \text{ and } u = \dot{\theta} \qquad \text{Eq. (18)}$$

The time derivative of the state variables P and $\theta$ are given by Equation (19) as follows:

$$\frac{dx_1}{dt} = \frac{dP}{dt} = F_1(\vec{x}, u) = F(P, \theta, \dot{\theta}) \qquad \text{Eq. (19)}$$

$$\frac{dx_2}{dt} = \frac{d\theta}{dt} = \dot{\theta}$$

The time derivative of the state vector is zero at the set point is shown in the following Equation (20):

$$\left.\frac{dx_1}{dt}\right|_{(\vec{x}=\vec{x}_0, u=0)} = F(P_0, \theta_0, 0) = 0 \qquad \text{Eq. (20)}$$

$$\left.\frac{dx_2}{dt}\right|_{(\vec{x}=\vec{x}_0, u=0)} = 0$$

The perturbations of the state variables are defined below in Equation (21). The derivative of the perturbed state is taken by expanding Equation (21) in a Taylor's series to obtain Equation (22), below, from Equation (19) and neglecting higher order terms.

$$\delta \vec{x} = \vec{x} - \vec{x}_0 \qquad \text{Eq. (21)}$$

$$\frac{d(\delta \vec{x})}{dt} = \left.\frac{\partial F}{\partial P}\right|_{X_0} \delta P + \left.\frac{\partial F}{\partial \theta}\right|_{X_0} \delta \theta + \left.\frac{\partial F}{\partial \dot{\theta}}\right|_{X_0} \delta \dot{\theta} \qquad \text{Eq. (22)}$$

The vector matrix form is:

$$\frac{d(\delta \vec{x})}{dt} = \frac{d}{dt}\begin{bmatrix} \delta P \\ \delta \theta \end{bmatrix} = A\begin{bmatrix} \delta P \\ \delta \theta \end{bmatrix} + B \delta u \qquad \text{Eq. (23)}$$

wherein:

$$A = \begin{bmatrix} \left.\frac{\partial F}{\partial P}\right|_{\overline{X}_0} & \left.\frac{\partial F}{\partial \theta}\right|_{\overline{X}_0} \\ 0 & 0 \end{bmatrix}, B = \begin{bmatrix} \left.\frac{\partial F}{\partial \dot{\theta}}\right|_{\overline{X}_0} \\ 1 \end{bmatrix}.$$

In a case wherein the squeeze pump is not working ($d_{uP}=0$), the nonlinear model of Equation (6) simplifies to the model of the following Equation (24) with variable fluidic resistance only.

$$\frac{dP}{dt} = -\left(\frac{1}{R_i C} + \frac{1}{(R_r + u_R(\theta))C}\right)P + \frac{P_r}{(R_r + u_R(\theta))C} \qquad \text{Eq. (24)}$$

Substituting Equation (24) into Equation (19), the linearized dynamics for the parameters in Table II of FIG. 9 are:

$$A = \begin{bmatrix} -0.046 & 35.1 \\ 0 & 0 \end{bmatrix}, B = \begin{bmatrix} 0 \\ 1 \end{bmatrix}, C = [1 \ 0], D = [0] \qquad \text{Eq. (25)}$$

The transfer function from the angular velocity of the motor $\dot{\theta}$ to the pressure P at second inlet 224 to microfluidic channel network 208 is:

$$\frac{P(s)}{\dot{\theta}(s)} = C(sI - A)^{-1}B = \frac{35.1}{s(s + 0.046)} \qquad \text{Eq. (26)}$$

The transfer function $G_R(s)$ from the motor angle $\theta$ to the pressure P at the inlet to the microfluidic channel network 208 is:

$$G_R(s) = \frac{P(s)}{\theta(s)} = s\frac{P(s)}{\dot{\theta}(s)} = \frac{35.1}{s + 0.046} \qquad \text{Eq. (27)}$$

Equation (28), below, is the dynamic equation for pressure when the variable resistance and squeeze pump are coupled.

$$\frac{dP}{dt} = -\left(\frac{1}{R_i C} + \frac{1}{(R_r + u_R(\theta))C}\right)P + \frac{P_r}{(R_r + u_R(\theta))C} - \frac{1}{C}\frac{dV_g(\theta)}{d\theta}\dot{\theta} \qquad \text{Eq. (28)}$$

Substituting Equation (28) into Equation (19), the linearized dynamics for the parameters in Table II of FIG. 9 are:

$$A = \begin{bmatrix} -0.046 & 35.1 \\ 0 & 0 \end{bmatrix}, B = \begin{bmatrix} 713 \\ 1 \end{bmatrix}, C = [1\ 0], D = [0] \quad \text{Eq. (29)}$$

The transfer function from the angular velocity of the motor $\dot{\theta}$ to the pressure P at inlet 224 to microfluidic channel network 208 is:

$$\frac{P(s)}{\dot{\theta}(s)} = C(sI - A)^{-1}B = \frac{713s + 35.1}{s(s + 0.046)} \quad \text{Eq. (30)}$$

The transfer function $G_{RP}(s)$ from the motor angle θ to the pressure P at the inlet to the microfluidic channel is simply $$G_{RP}(s) = \frac{P(s)}{\theta(s)} = s\frac{P(s)}{\dot{\theta}(s)} = \frac{713s + 35.1}{s + 0.046} = 713\frac{s + 0.049}{s + 0.046} \quad \text{Eq. (21)}$$

$G_R(s)$ and $G_{RP}(s)$ both have the same DC gain, but the squeeze pump provides derivative action indicated by the term 713 s. This results in a zero at −0.049 that nearly cancels the pole at −0.046. The system behavior can be illustrated by simulating the pressure responses to a constant acceleration pulse using the transfer functions of the two models: $G_R(s)$ (variable resistance only) in Equation (27) and $G_{RP}(s)$ (mechanically coupled variable resistance and squeeze pump) in Equation (31). As shown in graph 1000 of FIG. 10, when a constant acceleration pulse input signal of 2 sec. period was applied to motor 316 of VRVV modulator 300 of FIG. 3, the angular acceleration, angular velocity, and angular position of flywheel 332 were as represented, respectively, by lines 100A, 1008, 1012 in FIG. 10A. With the coupled variable resistance of narrow first tube 308 and variable volume of variable-volume second tube 312, the speed of the response is very fast (see line 1020 of graph 1024 of FIG. 10B) compared to the case with variable resistance only (see line 1028 in graph 1024 of FIG. 10B) due to the effect of the zero at −0.0493.

Controller Design

The physical parameters used in DC motor 316 and other components of VRVV modulator 300 are shown in Table III of FIG. 11. The specifications of motor 316 (GM9236 (5.9:1 Reduction Gear Ratio), Pittman, USA) were given and the parameters of the other components were estimated. Using these parameters, the transfer function of motor 316 is given by the following Equation (32) as an input of the voltage V applied to the motor and an output of the motor angle θ:

$$\frac{\theta(s)}{V(s)} = \frac{K_t}{\Delta(s)} \quad \text{Eq. (32)}$$

wherein:

$$\Delta(s) = J_{eq}L_m s^3 + (J_{eq}R_m + L_m B_{eq})s^2 + \quad \text{Eq. (33)}$$
$$(B_{eq}R_m + K_d L_m + K_t^2)s + K_d R_m$$

with.

$$J_{eq} = J_m + J_d, B_{eq} = B_m + B_d$$

-continued
$$G_M(s) = \frac{1.1E5}{(s + 1332)(s^2 + 324s + 32250)}$$

Equations (31) and (33) imply that the open-loop transfer function from voltage input to pressure the pressure at second inlet 224 is:

$$G_{SYS}(s) = G_M(s)G_{RP}(s) \quad \text{Eq. (34)}$$
$$= \frac{7.83E7(s + 0.049)}{(s + 0.046)(s + 1332)(s^2 + 324s + 32250)}$$

Exemplary specifications for control system performance are:
  Zero steady-state error for a step input;
  Overshoot less than 1 percent; and
  Closed-loop −3 dB Bandwidth—less than 1/10 of sensor sampling rate To eliminate steady-state error, controller 280 must have an integrator. Pressure sensors 292A-C employed in one example can report pressure measurements no faster than 125 Hz. To assure that the continuous-time controller design used is still valid when implemented in discrete-time at this sample rate, the design accounted for a closed-loop −3 dB bandwidth of less than 12.5 Hz. The design relies on the approximation that the closed-loop bandwidth is twice the open-loop 0 dB crossover frequency, which should be less than 6 Hz or 35 rad/s.

Figure 12A:
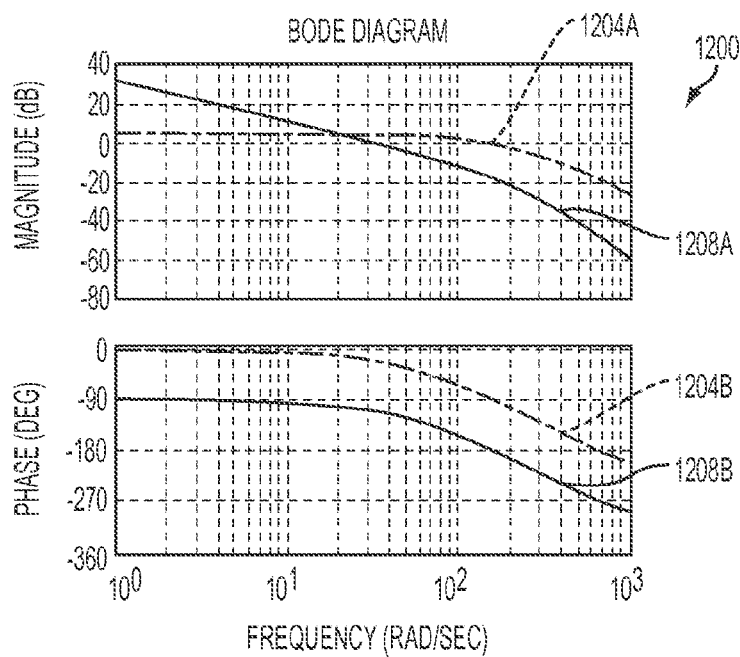
FIG. 12A is a Bode plot of the transfer function, $G_{SYS}(s)$, for uncompensated and compensated systems.

When an integrator is cascaded with the transfer function, $G_{SYS}(S)$, the phase is −112° at 35 rad/s, as illustrated in Bode plot 1200 of FIG. 12A. (In FIG. 12A, dotted lines 1204A-B represent an uncompensated system, and solid lines 1208A-B represent a compensated system.) Based on this, the integral controller of Equation (35) was chosen. Equation (35) provides the necessary gain for $\omega_{odB}$=35 rad/s. An integral controller is preferred over a proportional-integral controller for noise attenuation above the bandwidth frequency.

$$C_{SYS}(s) = \frac{19.5}{s} \quad \text{Eq. (35)}$$

The closed-loop transfer function with the compensator $C_{SYS}$ is:

$$G_{CL}(s) = \frac{1.53E9}{(s + 7.9)(s + 1332)(s^2 + 316s + 29596)} \quad \text{Eq. (36)}$$

Figure 12B:
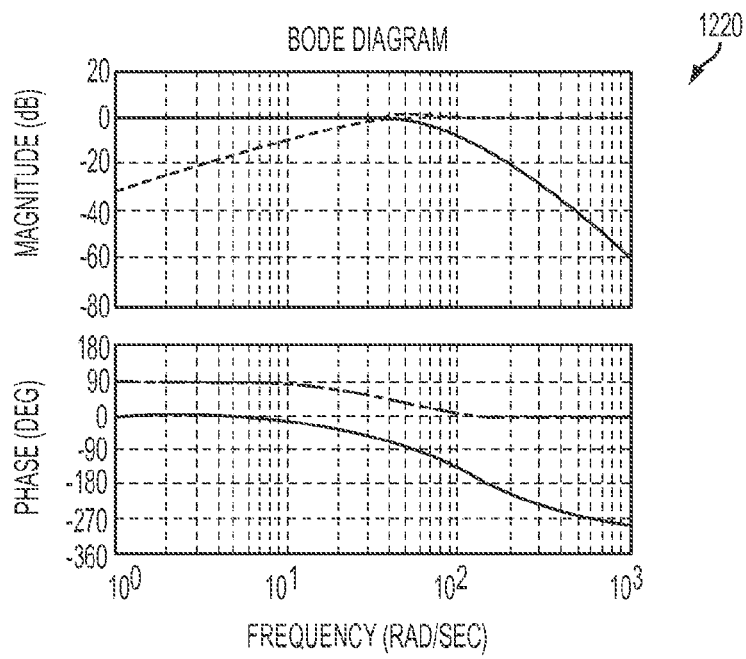
FIG. 12B is a Bode plot of a closed-loop system with a compensator.
Figure 12C:
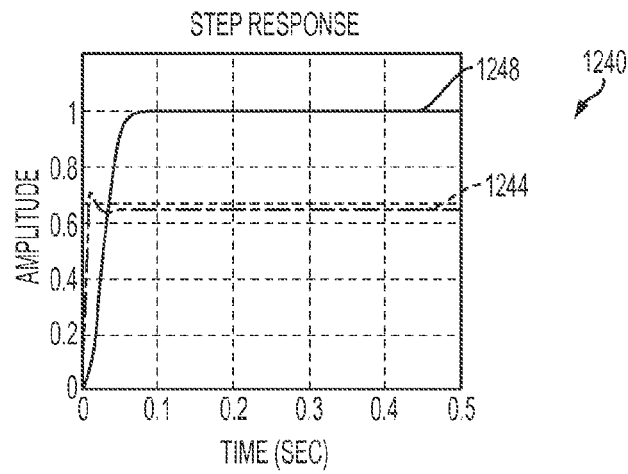
FIG. 12C is a plot of step responses for uncompensated and compensated closed-loop systems.

FIG. 12B shows a Bode plot 1220 of the closed-loop system. FIG. 12C is a graph 1240 showing the step response of the uncompensated (dotted line 1244) and compensated closed-loop system (solid line 1248), showing that the linearized dynamics satisfy the specifications.

Simulation Results

Figure 13:
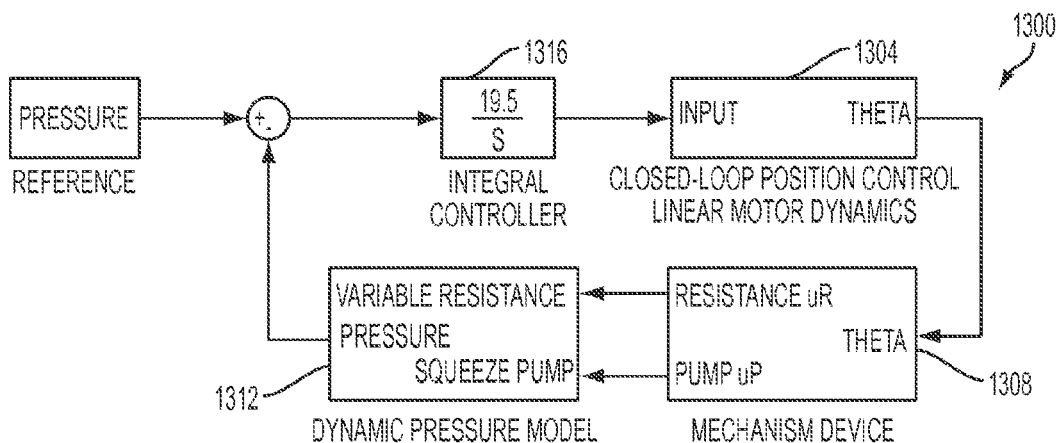
FIG. 13 is a diagram illustrating a computer-based model used to model a non-linear version of the VRVV modulator of FIGS. 3A-B.
Figure 14A:
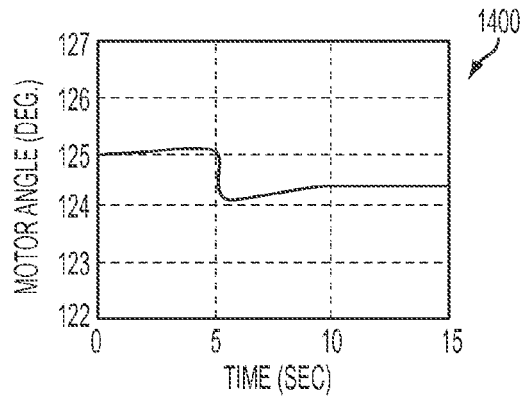
FIGS. 14A-D are graphs showing computer modeling results for, respectively, motor angle, variable resistance, squeeze pump flow rate, and regulated/reference pressures.
Figure 14B:
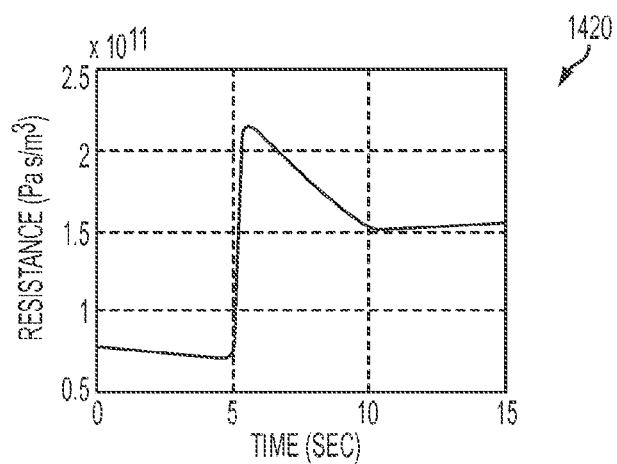
Figure 14C:
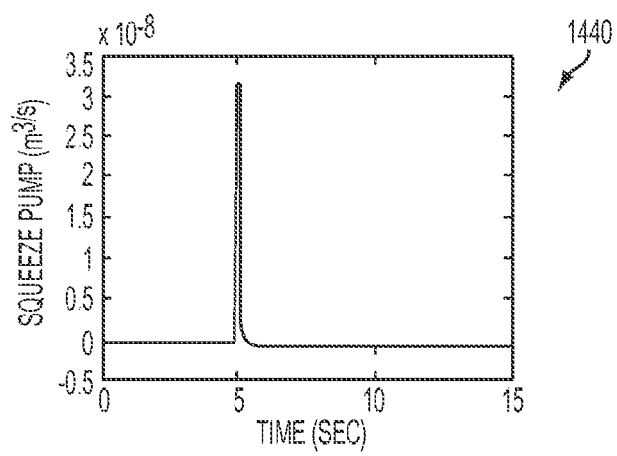
Figure 14D:
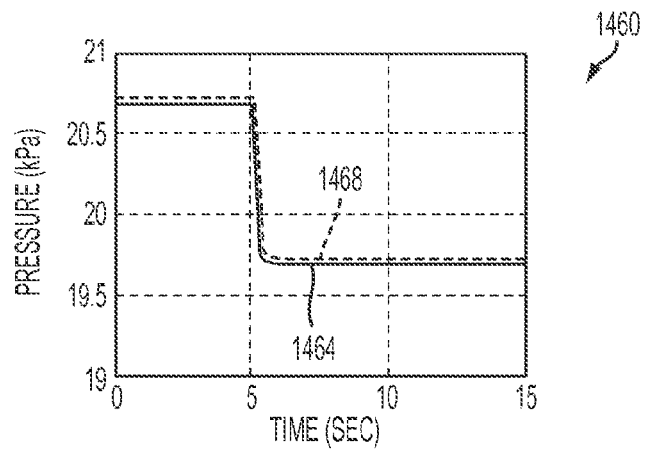

Simulations of VRVV modulator 300 of FIGS. 3A-B were performed for the nonlinear system version that included variable resistance and squeeze pump using MATLAB® and SIMULINK® software available from The MathWorks, Inc., Natick, Mass. FIG. 13 shows the SIMULINK® model 1300 for the system, which consists of a motor block 1304, a mechanism device block 1308 to produce variable resistance and squeeze pump, and a dynamic pressure model block 1312. The same compensator 1316 was applied to the control system as Equation (35). The reference pressure was set as a pressure decrease from 20.7 kPa to 19.7 kPa at 5 seconds. Graph 1400 of FIG. 14A shows the simulation results for the motor angle, graph 1420 of FIG. 14B shows the simulation results for the fluidic resistance, graph 1440 of FIG. 14C shows the simulation results for the flow rate of the squeeze pump, and graph 1460 shows the simulation results for the pressure response over time (solid line 1464 represents the regulated pressure, and dotted line 1468 represents the reference pressure). Line 1464 representing the regulated pressure displays no overshoot and no steady-state error, and the time to reach the steady-state value is less than 1 second for the decrease in pressure.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system, comprising:
  a variable-resistance variable-volume (VRVV) fluid-pressure regulator designed and configured to be fluidly connected to an inlet of a fluidic network or fluidic device upstream of the fluidic network or fluidic device, said VRVV fluid-pressure regulator including:
    a fluid path;
    a variable resistor located in the fluid path;
    a variable-volume reservoir structure that includes a variable-volume reservoir in fluid communication with said fluid path downstream of said variable resistor and having a volume;
    a controller in operative communication with said variable resistor and said variable-volume reservoir structure and including:
      a microprocessor; and
      a memory in operative communication with said microprocessor to allow said microprocessor to execute machine-executable instructions stored in said memory, said memory containing:
        a first set of machine-executable instructions for receiving a signal from a pressure sensor located downstream of said variable-volume reservoir; and
        a second set of machine-executable instructions for executing a pressure control algorithm designed and configured to generate, as a function of the signal, at least one control signal designed and configured for modulating pressure of the fluid at the inlet of the fluidic network or fluidic device by:
          controlling, via said controller, said variable resistor to controllably change in a determined direction, either increasing or decreasing, resistance to flow of the fluid through said variable resistor along said flow path; and
          controlling, via said controller, said variable-volume reservoir structure to controllably change in the determined direction said volume of said variable-volume reservoir structure simultaneously with changing said resistance of said variable-volume resistor.

2. A system according to claim 1, wherein said second set of machine-executable instructions includes, for increasing pressure of the fluid at the inlet of the fluidic network or fluidic device, machine-executable instructions for controlling the variable resistor to decrease the resistance and machine-executable instructions for controlling the variable-volume reservoir structure to decrease the volume.

3. A system according to claim 1, wherein said second set of machine-executable instructions includes, for decreasing pressure of the fluid at the inlet of the fluidic network or fluidic device, machine-executable instructions for controlling the variable resistor to increase the resistance and machine-executable instructions for controlling the variable-volume reservoir structure to increase the volume.

4. A system according to claim 1, further comprising machine-executable instructions for measuring a first pressure in the fluid at a first location upstream of said VRVV fluid-pressure regulator and for measuring a second pressure in the fluid at a second location downstream of said VRVV fluid-pressure regulator, wherein said second set of machine-executable instructions includes machine-executable instructions that execute a control algorithm designed and configured to generate the at least one control signal as a function of both the first and second pressures.

5. A system according to claim 1, wherein said variable resistor includes a first flexible-walled tube carrying the fluid and said second set of machine-executable instructions includes machine-executable instructions for changing an extent of transverse compression of said first flexible-walled tube.

6. A system according to claim 5, wherein said variable-volume reservoir comprises a second flexible-walled tube and said second set of machine-executable instructions includes machine-executable instructions for changing an extent of transverse compression of said second flexible-walled tube.

7. A system according to claim 1, further comprising a single actuator mechanism in operative communication with each of said variable resistor and said variable-volume reservoir structure, wherein said second set of machine-executable instructions further comprise machine-executable instructions for controlling said single actuator mechanism so as to actuate each of said variable resistor and said variable-volume reservoir structure.

8. A system according to claim 7, wherein said single actuator mechanism includes a multi-link mechanical-linkage mechanism and said machine-executable instructions for controlling said single actuator mechanism includes machine-executable instructions for controlling said multi-link mechanical-linkage mechanism so as to actuate each of said variable resistor and said variable-volume reservoir structure.

9. A system according to claim 1, wherein the fluidic network or fluidic device is a multi-inlet device having a first inlet receiving a first fluid and a second inlet receiving a second fluid, said machine-executable instructions further comprising machine-executable instructions for receiving a first pressure signal representing pressure of the first fluid at the first inlet and a second pressure signal representing pressure of the second fluid at the second inlet, and said second set of machine-executable instructions including machine-executable instructions for executing a control algorithm designed and configured to generate the at least one control signal for controlling the first pressure as a function of the first and second pressures.

10. A system according to claim 1, wherein said variable-volume reservoir is fluidly branched off of the fluid path between said variable resistor and the inlet of the fluidic network or fluidic device.

* * * * *

UNITED STATES PATENT AND TRADEMARK OFFICE
CERTIFICATE OF CORRECTION

| | | |
|---|---|---|
| PATENT NO. | : 9,625,918 B2 | Page 1 of 1 |
| APPLICATION NO. | : 14/857290 | |
| DATED | : April 18, 2017 | |
| INVENTOR(S) | : Yong-Tae Kim et al. | |

It is certified that error appears in the above-identified patent and that said Letters Patent is hereby corrected as shown below:

In the Specification

Replace the paragraph beginning at Column 1, Line 21, as follows:
This invention was made with United States government support under CMS0555513 awarded by the National Science Foundation. The U.S. government has certain rights in the invention.

Signed and Sealed this
Tenth Day of May, 2022

Katherine Kelly Vidal
*Director of the United States Patent and Trademark Office*